United States Patent
Gaines et al.

(10) Patent No.: US 11,051,701 B1
(45) Date of Patent: Jul. 6, 2021

(54) METHODS, SYSTEMS, AND COMPUTER READABLE MEDIA FOR OBTAINING ACCURATE SKIN TEMPERATURE MEASUREMENTS

(71) Applicant: Clairvoyant Networks, Inc., Austin, TX (US)

(72) Inventors: Robert Bradley Gaines, Lake Saint Louis, MO (US); Stephen Edward Popovich, Austin, TX (US); Aaron Murdoch, Colorado Springs, CO (US)

(73) Assignee: CLAIRVOYANT NETWORKS, INC., Austin, TX (US)

( * ) Notice: Subject to any disclaimer, the term of this patent is extended or adjusted under 35 U.S.C. 154(b) by 0 days.

(21) Appl. No.: 17/083,252

(22) Filed: Oct. 28, 2020

(51) Int. Cl.
*G06K 9/00* (2006.01)
*A61B 5/01* (2006.01)
*H04N 7/18* (2006.01)
*G06T 7/73* (2017.01)
*G01J 5/12* (2006.01)
(Continued)

(52) U.S. Cl.
CPC .............. *A61B 5/015* (2013.01); *A61B 5/743* (2013.01); *G01J 5/0025* (2013.01); *G01J 5/12* (2013.01); *G06T 7/73* (2017.01); *H04N 7/183* (2013.01); *A61B 2562/0271* (2013.01); *G06T 2207/30201* (2013.01)

(58) Field of Classification Search
None
See application file for complete search history.

(56) References Cited

U.S. PATENT DOCUMENTS

| | | | |
|---|---|---|---|
| 8,275,413 B1* | 9/2012 | Fraden | G01J 1/0233 455/556.1 |
| 10,895,506 B1* | 1/2021 | Lander | G01J 5/047 |

(Continued)

OTHER PUBLICATIONS

"Flir A700 Complete Smart Sensor Camera System," https://www.midstateinstruments.com/infrared-cameras/flir-a700-complete-smart-sensor-camera-system/, 4 pages (2020).
(Continued)

*Primary Examiner* — Shervin K Nakhjavan
(74) *Attorney, Agent, or Firm* — Jenkins, Wilson, Taylor & Hunt, P.A.

(57) ABSTRACT

A method for obtaining accurate skin temperature measurements includes displaying, on a display, a video image of a temperature measurement subject captured by a camera. The method further includes displaying, on the display, at least one visual alignment cue sized and positioned on the display such that when a predetermined portion of the video image of the subject is aligned with the at least one visual alignment cue, the subject is located at a predetermined distance and orientation for accurate skin temperature measurement by a contactless temperature sensor. The method further includes analyzing the video image of the subject and detecting when the predetermined portion of the video image of the subject is aligned with the at visual alignment cue. The method further includes triggering the contactless temperature sensor to record a skin temperature measurement of the subject when the predetermined portion of the video image of the subject is aligned with the at least one visual alignment cue.

30 Claims, 13 Drawing Sheets

(51) Int. Cl.
   *A61B 5/00*   (2006.01)
   *G01J 5/00*   (2006.01)

(56) References Cited

U.S. PATENT DOCUMENTS

| | | | |
|---|---|---|---|
| 2012/0086810 A1* | 4/2012 | Messerschmid | G01J 5/0265 |
| | | | 348/164 |
| 2016/0206216 A1* | 7/2016 | Kirenko | A61B 5/14551 |
| 2016/0262629 A1* | 9/2016 | Abreu | A61B 5/01 |
| 2016/0345832 A1* | 12/2016 | Pavagada Nagaraja | |
| | | | A61B 5/746 |
| 2018/0238740 A1* | 8/2018 | Christel | G01J 5/0275 |

OTHER PUBLICATIONS

"Increase Safety with Elo Access™," https://www.elotouch.com/elo-access, 8 pages (2020).

"Non-Contact Infrared Thermometer, IR 300," https://www.medsourcelabs.com/product/non-contact-infrared-thermometer-ir-300/, pp. 5 (2020).

\* cited by examiner

| SKIN LOCATION | COLD (15°C) | ROOM (27°C) | HOT (47°C) |
|---|---|---|---|
| FOREHEAD (A) | 31.7 | 35.2 | 37 |
| BACK OF NECK (B) | 31.2 | 35.1 | 36.1 |
| CHEST (C) | 30.1 | 34.4 | 35.8 |
| UPPER BACK (D) | 30.7 | 34.4 | 36.3 |
| LOWER BACK (E) | 29.2 | 33.7 | 36.6 |
| UPPER ABDOMEN (F) | 29.0 | 33.8 | 35.7 |
| LOWER ABDOMEN (G) | 29.2 | 34.8 | 36.2 |
| TRICEP (H) | 28.0 | 33.2 | 36.6 |
| FOREARM (J) | 26.9 | 34.0 | 37.0 |
| HAND (L) | 23.7 | 33.8 | 36.7 |
| HIP (M) | 26.5 | 32.2 | 36.8 |
| SIDE THIGH (N) | 27.3 | 33.0 | 36.5 |
| FRONT THIGH (O) | 29.4 | 33.7 | 36.7 |
| BACK THIGH (P) | 25.5 | 32.2 | 36.0 |
| CALF (Q) | 25.1 | 31.6 | 35.9 |
| FOOT (R) | 23.2 | 30.4 | 36.2 |

| TEMPERATURE SITE | NORMAL BODY TEMPERATURE BY PATIENTS AGE | | | |
|---|---|---|---|---|
| | 0-2 YEARS | 3-10 YEARS | 11-65 YEARS | >65 YEARS |
| EAR | 97.5°-100.4°F 36.3°-38.0°C | 97.0°-100.0°F 36.1°-37.7°C | 96.6°-99.7°F 35.8°-37.6°C | 96.4°-99.5°F 35.7°-37.5°C |
| ORAL | | 95.9°-99.5°F 35.3°-37.5°C | 97.6°-99.6°F 36.7°-37.8°C | 96.4°-98.5°F 35.7°-36.9°C |
| CORE | 97.5°-100.0°F 36.3°-37.7°C | 97.5°-100.0°F 36.3°-37.7°C | 98.2°-100.2°F 36.7°-37.8°C | 96.6°-98.8°F 35.8°-37.1°C |
| RECTAL | 97.9°-100.4°F 36.6°-38.0°C | 97.9°-100.4°F 36.5°-38.0°C | 98.6°-100.6°F 37.0°-38.1°C | 97.1°-99.2°F 36.1°-37.3°C |
| AXILLARY | 94.5°-99.1°F 34.7°-37.2°C | 96.6°-98.0°F 35.8°-36.6°C | 95.3°-98.4°F 35.1°-36.8°C | 96.0°-97.4°F 35.5°-36.3°C |

EAR AVERAGE IS 98.2F

ORAL AVERAGE IS 98.6F

CORE AVERAGE IS 99.2F

RECTAL AVERAGE IS 99.6F

AXILLARY AVERAGE IS 96.9F

FIG. 13

| | | |
|---|---|---|
| ○ | FOREHEAD | 0F |
| ⦸ | ORAL | 0.56F |
| ○ | RECTAL | 1.56F |
| ○ | EAR | 0.16F |
| ○ | CORE | 1.16F |
| ○ | AXILLARY | -1.14F |

FIG. 14

METHODS, SYSTEMS, AND COMPUTER READABLE MEDIA FOR OBTAINING ACCURATE SKIN TEMPERATURE MEASUREMENTS

TECHNICAL FIELD

The subject matter described herein relates to obtaining skin temperature measurements of subjects. More particularly, the subject matter described here in relates to methods, systems, and computer readable media for obtaining accurate skin temperature measurements of subjects.

BACKGROUND

Skin temperature measurements are becoming increasingly prevalent in screening subjects for medical conditions. For example, skin temperature measurements are used as a rapid screening tool to indicate whether a subject's core body temperature is above normal. An elevated skin temperature measurement can be used as an indicator that the subject has a fever and therefore requires further screening to determine whether an underlying medical condition, such as COVID-19, exists.

Skin temperature measurements can be obtained using an infrared temperature sensor that measures the temperature of the skin on a subject's forehead. One problem with using an infrared temperature sensor to measure skin temperature is that the recorded temperatures vary widely with position and orientation of the sensor with regard to the area of the subject's skin used for the temperature measurement, which is typically the subject's forehead. The wide variance in sensor position in making skin temperature measurements makes measurement results difficult to interpret. For example, if the sensor is located outside of the range specified by the manufacturer of a particular temperature sensor for skin temperature measurements, then measurements made by the sensor may be inaccurate (i.e., too low or too high).

In light of these and other difficulties, there exists a need for improved methods, systems, and computer readable media for obtaining accurate skin temperature measurements of subjects.

SUMMARY

A method for obtaining accurate skin temperature measurements includes displaying, on a display, a video image of a temperature measurement subject captured by a camera. The method further includes displaying, on the display, at least one visual alignment cue sized and positioned on the display such that when a predetermined portion of the video image of the subject is aligned with the at least one visual alignment cue, the subject is located at a predetermined distance and orientation for accurate skin temperature measurement by a contactless temperature sensor. The method further includes analyzing the video image of the subject and detecting when the predetermined portion of the video image of the subject is aligned with the at visual alignment cue. The method further includes triggering the contactless temperature sensor to record a skin temperature measurement of the subject when the predetermined portion of the video image of the subject is aligned with the at least one visual alignment cue.

According to another aspect of the subject matter described herein, the at least one visual alignment cue is sized such that alignment of the predetermined portion of the video image of the subject with the at least one visual alignment cue is indicative of the subject being at a distance from the contactless temperature sensor that is within a specified tolerance of the contactless temperature sensor for recording the skin temperature measurement of the subject.

According to another aspect of the subject matter described herein, the at least one visual alignment cue is positioned on the display to vertically and horizontally align a portion of the subject's skin within a field of view of the temperature sensor.

According to another aspect of the subject matter described herein the skin temperature measurement is output as an absolute temperature.

According to another aspect of the subject matter described herein the method for accurate skin temperature measurements includes determining an average skin temperature of a plurality of subjects in a given ambient environment, comparing the skin temperature measurement of the subject to the average skin temperature.

According to another aspect of the subject matter described herein, the method for accurate skin temperature measurements generating output indicating that the subject possibly has a fever when the skin temperature measurement of the subject exceeds the average skin temperature by more than a threshold amount.

According to another aspect of the subject matter described herein, displaying the at least one visual alignment cue for aligning at least a portion of the image of the subject with the visual alignment cue displaying virtual objects for aligning eyes of the subject with the virtual objects.

According to another aspect of the subject matter described herein, the virtual objects comprise geometric shapes.

According to another aspect of the subject matter described herein the method for accurate skin temperature measurements includes displaying a visual indicator to the subject when the at least a portion of the image of the subject is aligned with the at least one visual alignment cue.

According to another aspect of the subject matter described herein displaying the at least one visual alignment cue includes displaying the at least one visual alignment cue as a moving virtual object, further comprising prompting the subject to move to maintain alignment between the predetermined portion of the image of the subject and the at least one moving virtual object, and wherein triggering the temperature sensor to obtain the skin temperature measurement includes triggering the temperature sensor to record plural skin temperature measurements as the subject moves to maintain the alignment. In one example, a peak skin temperature measurement is reported, where the peak skin temperature measurement is an average of the three highest skin temperature measurement obtained as the subject moves to maintain the alignment with the moving virtual object.

According to another aspect of the subject matter described herein, the display is a component of a stand-alone kiosk lacking wireless connectivity and that includes the display, the camera, and the temperature sensor and the method for accurate skin temperature measurements includes displaying a first quick response (QR) code on the display for directing a mobile device of the subject to a website for obtaining identity and health information from the subject, receiving, via the website and from the subject via the mobile device, the identity and health information, encoding the identity and health information in a second QR code and displaying the second QR code on the mobile device, reading, by the camera, the second QR code, and, in response, prompting the subject to initiate the process for allowing the contactless temperature sensor to obtain the skin temperature measurement of the subject, encoding the skin temperature measurement and the identity and health information in a third QR code, displaying the third QR code on the display, prompting the subject to scan the third QR code using the mobile device, and in response to the subject scanning the third QR code, uploading the identity and health information and the skin temperature measurement from the mobile device to a database.

According to another aspect of the subject matter described herein, a system for obtaining accurate skin temperature measurements includes a housing. The system further includes a contactless temperature sensor located in the housing. The system further includes a camera located in the housing at a fixed distance with respect to the contactless temperature sensor. The system further includes a display for displaying a video image of a temperature measurement subject captured by the camera. The system further includes a computing platform including at least one processor and a memory. The system further includes a display controller and measurement trigger generator implemented by the at least one processor and configured to display, on the display, at least one visual alignment cue sized and positioned on the display such that when a predetermined portion of the video image of the subject is aligned with the at least one visual alignment cue, the subject is located at a predetermined distance and orientation for accurate skin temperature measurement by the contactless temperature sensor, analyze the video image of the subject and detecting when the at predetermined portion of the video image of the subject is aligned with the at visual alignment cue, and trigger the contactless temperature sensor to record a skin temperature measurement of the subject when the predetermined portion of the video image of the subject is aligned with the at least one visual alignment cue.

According to another aspect of the subject matter described herein, the display controller and measurement trigger generator is configured to size the at least one visual alignment cue such that alignment of the predetermined portion of the video image of the subject with the at least one visual alignment cue is indicative of the subject being at a distance from the contactless temperature sensor that is within a specified tolerance of the contactless temperature sensor for recording the skin temperature measurement of the subject.

According to another aspect of the subject matter described herein, the display controller and measurement trigger generator is configured to position the at least one visual alignment cue on the display to vertically and horizontally align a portion of the subject's skin within a field of view of the temperature sensor.

According to another aspect of the subject matter described herein, the display controller and measurement trigger generator is configured to output the skin temperature measurement as an absolute temperature.

According to another aspect of the subject matter described herein, the display controller and measurement trigger generator is configured to determine an average skin temperature of a plurality of subjects in a given ambient environment, comparing the skin temperature measurement of the subject to the average skin temperature.

According to another aspect of the subject matter described herein, the display controller and measurement trigger generator is configured to generate output indicating that the subject possibly has a fever when the skin temperature measurement of the subject exceeds the average skin temperature by more than a threshold amount.

According to another aspect of the subject matter described herein, the display controller and measurement trigger generator is configured to display, as the at least one visual alignment cue, virtual objects for aligning eyes of the subject with the virtual objects.

According to another aspect of the subject matter described herein, the display controller and measurement trigger generator is configured to display a visual indicator to the subject when the at least a portion of the image of the subject is aligned with the at least one visual alignment cue.

According to another aspect of the subject matter described herein, the display controller and measurement trigger generator is configured to display the at least one visual alignment cue as a moving virtual object, to prompt the subject to move to maintain alignment between the predetermined portion of the image of the subject and the at least one moving virtual object and to trigger the temperature sensor to record plural skin temperature measurements as the subject moves to maintain the alignment. In one example, a peak skin temperature measurement is reported, where the peak skin temperature measurement is an average of the three highest skin temperature measurement obtained as the subject moves to maintain the alignment with the moving virtual object.

According to another aspect of the subject matter described herein, the contactless temperature sensor comprises an infrared temperature sensor.

According to another aspect of the subject matter described herein, the system for accurate temperature sensor measurements includes a stand-alone kiosk lacking wireless connectivity and wherein the display and the housing are coupled to the display and the display controller and measurement trigger generator is configured to display a first quick response (QR) code on the display for directing a mobile device of the subject to a website for obtaining identity and health information from the subject, read, from the camera, a second QR code including health and identification information received from the subject, prompt the subject to initiate the process for allowing the contactless temperature sensor to obtain the skin temperature measurement of the subject, encode the skin temperature measurement and the identity and health information in a third QR code, display the third QR code on the display, and prompt the subject to scan the third QR code using a mobile device for communication from the mobile device to a database.

According to another aspect of the subject matter described herein, a non-transitory computer readable medium having stored thereon executable instructions that when executed by a processor of a computer control the computer to perform steps is provided. The steps include displaying, on a display, a video image of a temperature measurement subject captured by a camera. The steps further include displaying, on the display, at least one visual alignment cue sized and positioned on the display such that when a predetermined portion of the video image of the subject is aligned with the at least one visual alignment cue, the subject is located at a predetermined distance and orientation for accurate skin temperature measurement by a contactless temperature sensor. The steps further include analyzing the video image of the subject and detecting when the predetermined portion of the video image of the subject is aligned with the at visual alignment cue. The steps further include triggering the contactless temperature sensor to record a skin temperature measurement of the subject when the predetermined portion of the video image of the subject is aligned with the at least one visual alignment cue.

The subject matter described herein may be implemented in hardware, software, firmware, or any combination thereof. As such, the terms "function" "node" or "module" as used herein refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which:

FIG. 13 is a table illustrating average ranges for converting between temperature measurement modes; and FIG. 14 is a diagram illustrating exemplary temperature measurement mode conversion factors calculated using the data in the table in FIG. 13 and at least one additional body temperature measurement.

DETAILED DESCRIPTION

Figure 1:
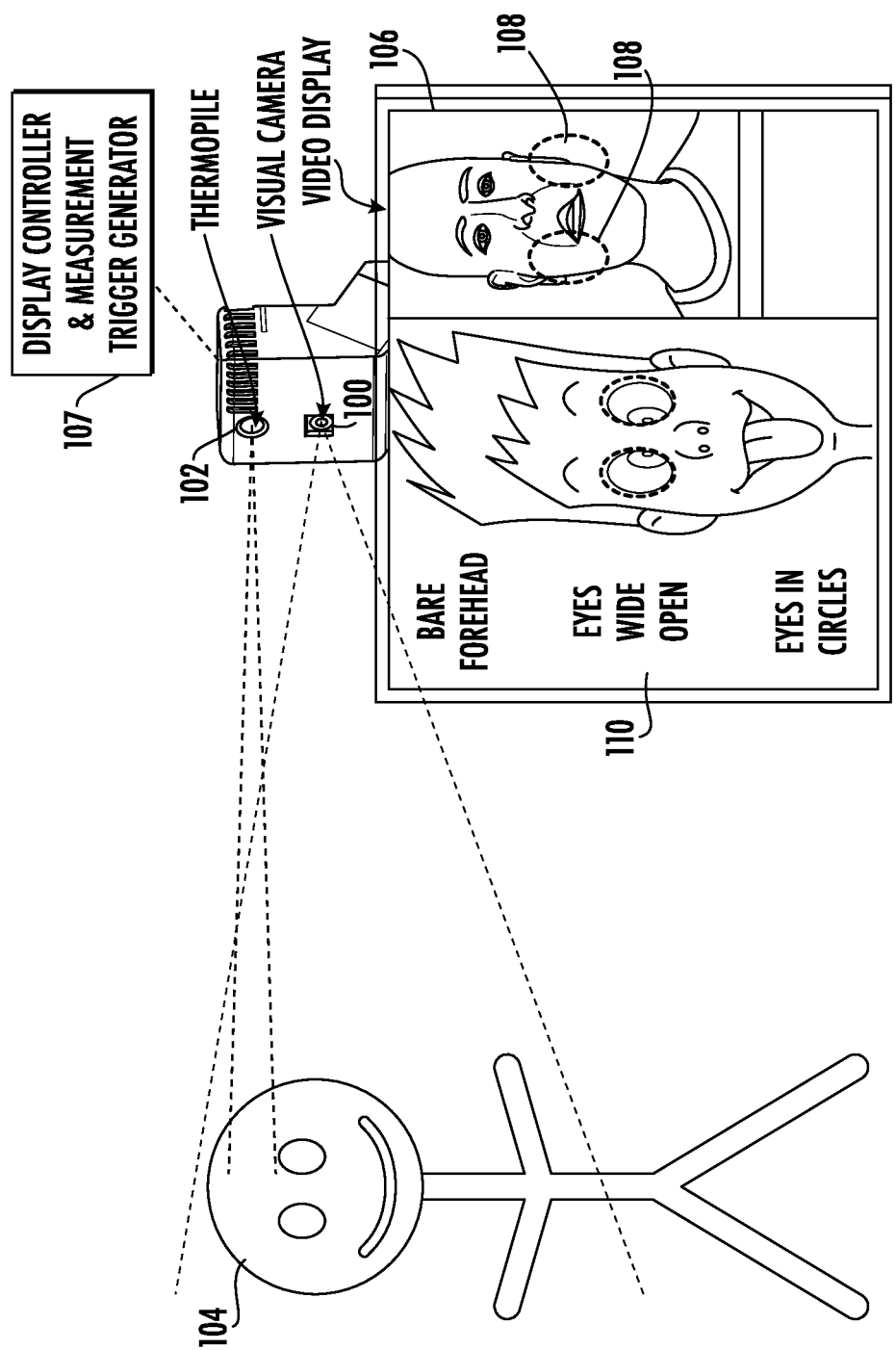
FIG. 1 is a schematic diagram illustrating an exemplary system for obtaining accurate skin temperature measurements of subjects.

The subject matter described here in relates to methods, systems and computer readable media for obtaining accurate skin temperature measurements of subjects. FIG. 1 is a schematic diagram illustrating exemplary components of a system for obtaining accurate skin temperature measurements of subjects. Referring to FIG. 1, the system includes a camera 100 and a temperature sensor 102 located at a fixed distance from camera 100 by virtue of the relative placement of camera 100 and sensor 102 within a housing 103. In the illustrated example, the fields of view of camera 100 and temperature sensor 102 are vertically aligned and are spaced from each other by a fixed vertical distance. Camera 100 may be a video camera designed to obtain a video image of a subject 104 for display on a video display 106.

Temperature sensor 102 may be any suitable sensor for obtaining a subject's skin temperature without touching the subject. In FIG. 1, temperature sensor 102 is an infrared sensor that includes a thermopile for generating a voltage indicative of a measured temperature difference. Using an infrared or other type of contactless temperature sensor requires that the temperature sensor be located at a measurement location that is within the field of view of the temperature sensor and located at a range that is within a tolerance specified by a manufacturer of the temperature sensor.

A display controller and measurement trigger generator 107 may display visual alignment cues 108 in the video image of the subject to prompt the subject to align the subject's eyes with visual alignment cues 108. When the subject aligns the subject's eyes with visual alignment cues 108, the display controller and measurement trigger generator 107 triggers temperature sensor 102 to record the skin temperature of the subject. Display controller and measurement trigger generator 107 may also display visual instructions 110 that instruct the subject as to how to use the video display to align the subject's eyes with visual alignment cues 108.

Figure 2A:
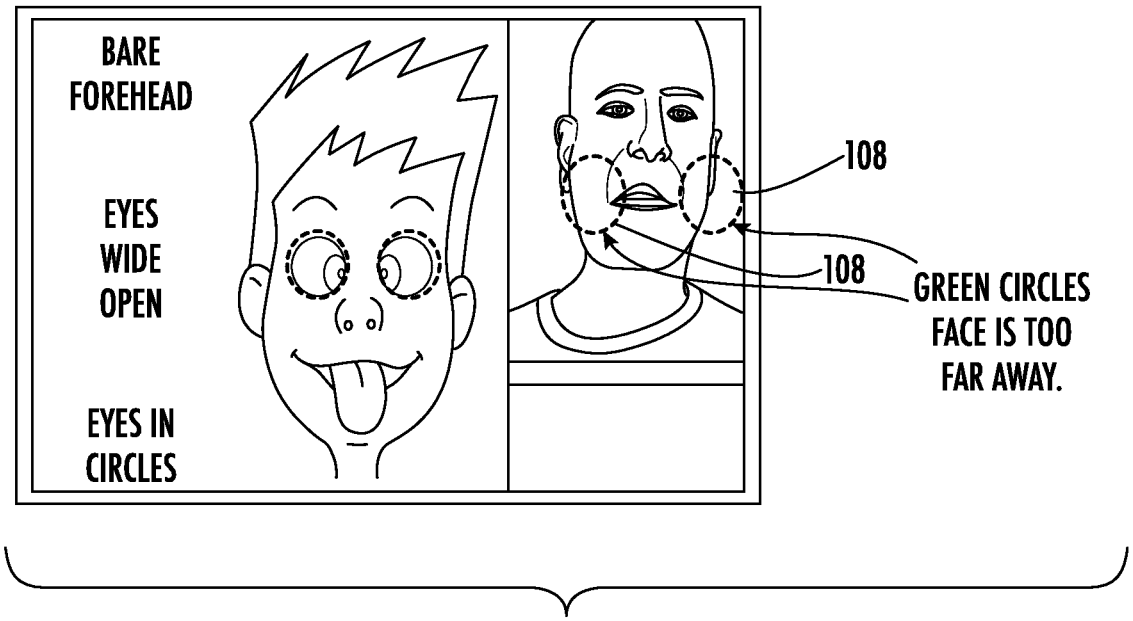
FIG. 2A is an image of a subject misaligned with visual alignment cues for obtaining accurate skin temperature measurements.
Figure 2B:
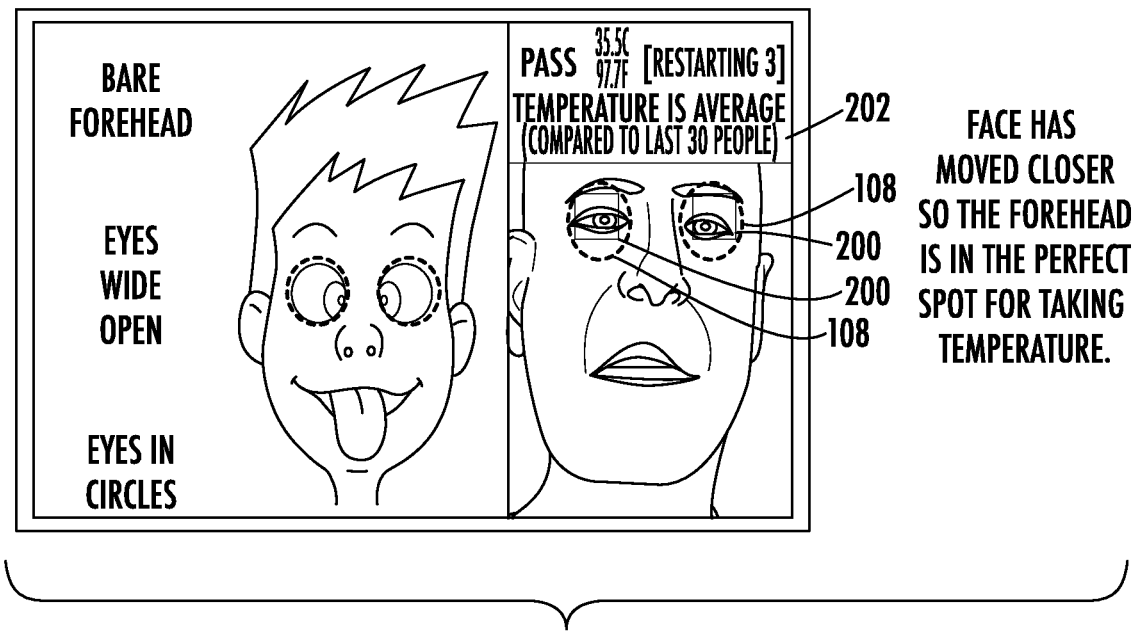
FIG. 2B is an image illustrating alignment of the subject's eyes with the visual alignment cues.

FIGS. 2A and 2B illustrate the alignment process in more detail. In FIG. 2A, the video image of subject is not aligned with the visual alignment cues 108. In FIG. 2B, the video image of the subject's eyes is aligned with visual alignment cues 108. When this occurs, display controller and measurement trigger generator 107 displays a visual alignment indicator 200 indicating proper alignment of the subject's eyes with visual alignment cues 108 and triggers sensor 102 to obtain a temperature measurement of the subject. In the illustrated example, visual alignment indicator 200 includes a pair of blue squares that surround the video image of subject's eyes. However, other visual indicators could be used to indicate proper alignment. In the illustrated example, display controller and measurement trigger generator 107 controls display 106 to display an indication 202 that the skin temperature of the subject is average when compared to the last 30 people and therefore the subject passes and does not require further screening. In addition, as will be described in detail below, display controller and measurement trigger generator 107 may also send a signal to a printer attached to the same kiosk as display 106 instructing the printer to print a badge identifying the subject and displaying results of the skin temperature measurement.

Figure 3:
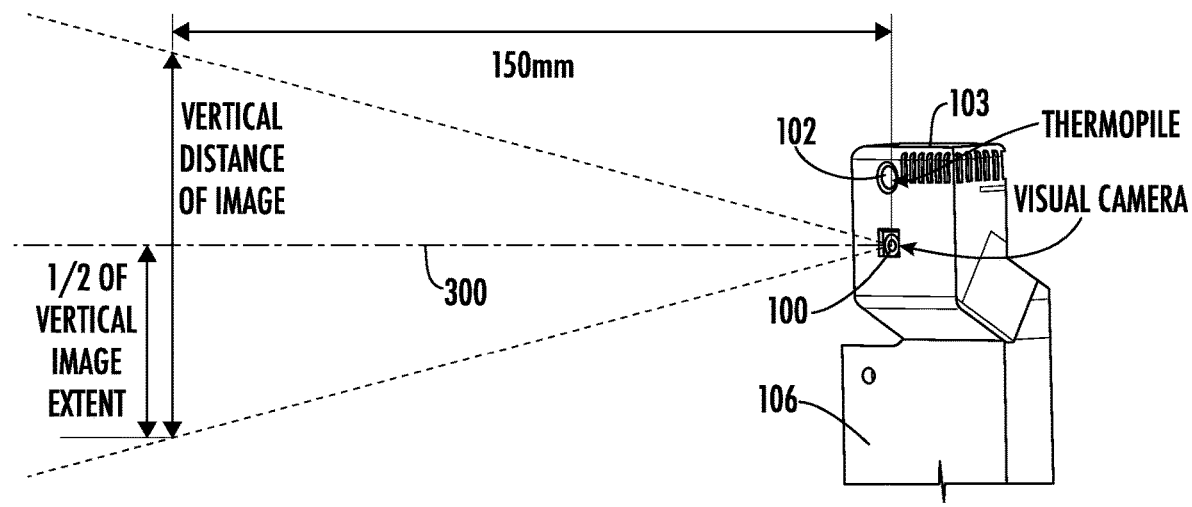
FIG. 3 is a schematic diagram illustrating exemplary dimensions used to determine positioning of the visual alignment cues on the display of FIGS. 2A and 2B for obtaining accurate skin temperature measurements of subjects.

FIG. 3 is a schematic diagram illustrating exemplary measurements used to determine the proper placement of visual alignment cues 108 such that the subject is spaced within manufacturer specifications for accurate temperature measurements by sensor 102. In FIG. 3, the optimal distance or range in front of sensor 102 for an accurate temperature measurement is assumed to be 150 millimeters.

In addition to locating the subject at the optimal range in front of the sensor, the subject's forehead should also be aligned vertically with the sensor. The camera field of view, the range, and the sensor field of view can be used to determine the proper placement of visual alignment cues 108 on display 106 for vertical alignment the subject. In the illustrated example, the field of view of camera 100 is assumed to be 30 degrees, and the field of view of temperature sensor 102 is assumed to be 5 degrees. The vertical image distance is found using Equation 1:

$$\tan\left(\frac{30}{2}\right) = \frac{((\text{vertical image})/2)}{150 \text{ mm}} \qquad (1)$$

In Equation 1, "vertical image" is the vertical extent of the image at the optimal range of 150 mm and labeled "vertical distance of image" in FIG. 3. Using the definition of a tangent, if the camera field of view if halved as indicated by dashed line 300 in FIG. 3, Equation 1 represents a relationship of the angle equal to half of the field of view of the camera and half of the vertical extent of the image. If Equation 1 is solved for "vertical image", the value for "vertical image" given the dimensions in FIG. 3 80 millimeters. Since the camera used in this implementation has 1080 vertical pixels, the display has 1080/80=13.5 pixels per millimeter. The vertical distance between sensor 102 and camera 104 is 20 millimeters. Therefore, the visual alignment cues are drawn at 20×13.5=270 pixels above the vertical center line of field of view of camera 100, which locates the circles at the horizontal center line of the field of view of sensor 102.

The size of the circles used as visual alignment cues 108 can be set to force the user to move the user's head the correct distance from sensor 102. In one exemplary implementation, it is assumed that the diameter of the human eye is relatively consistent for a given population of subjects. For purposes of discussion, 25 millimeters is used.

Display controller and measurement trigger generator 107 is configured to look for eyes which are 25 mm in diameter. Using the same ratio of 13.5 pixels per mm at the optimal distance or range from the display, display controller and measurement trigger generator 107 is programmed to find eyes which are 25×13.5=337 pixels in diameter. Stated differently, if the detected eye images are 337 pixels in diameter, then the eyes are located at the optimal range for temperature measurements by sensor 102. Accordingly, visual alignment cues 108 may each have an inner diameter that is equal to or approximately equal to 337 pixels.

Display controller and measurement trigger generator 107 allows for some tolerance around this number but for the sake of understanding, display controller and measurement trigger generator 107 may make the following determinations as the user moves in the field of view of camera 100:
(1) If the detected eye is much smaller than 337 pixels, the user is too far away.
(2) If the detected eye is much larger than 337 pixels, the user is too close.

In short, eye circles are drawn in the horizontal center of the image and 270 pixels up vertically from the center line of the camera. The size of the eye circles are drawn such that when the person's eyes fit the eye circles within a predetermined threshold, display controller and measurement trigger generator 107 may determine that the subject is at the correct distance and may generate a trigger signal that triggers temperature sensor 102 to obtain a skin temperature measurement of the subject.

To further improve the system, display controller and measurement trigger generator 107 has other filtering mechanisms. In addition to requiring the eyes to be a known number of pixels in size, we can also require the distance between the eyes to be within a certain range. We can also require the horizontal centers of both eyes to be level in the image. We can also require the midpoint between the eyes to be close to the midpoint of the two circles. All these additional software filters improve the performance and reliability of our eye detections (they prevent false detections).

All the math derivations given above are used for understanding purposes. In practice, display controller and measurement trigger generator 107 may be calibrated manually as follows.

The position of camera 100 and sensor 102 are fixed by the dimensions of housing 103. In one example, display controller and measurement trigger generator 107 is placed in test mode and we move a hot iron in front of camera 100 until sensor 102 registers a peak temperature reading. This point of peak temperature reading is then marked on the visual display and the eye circles used as visual alignment cues 108 are located on display 106 with reference to this location.

Figure 4:
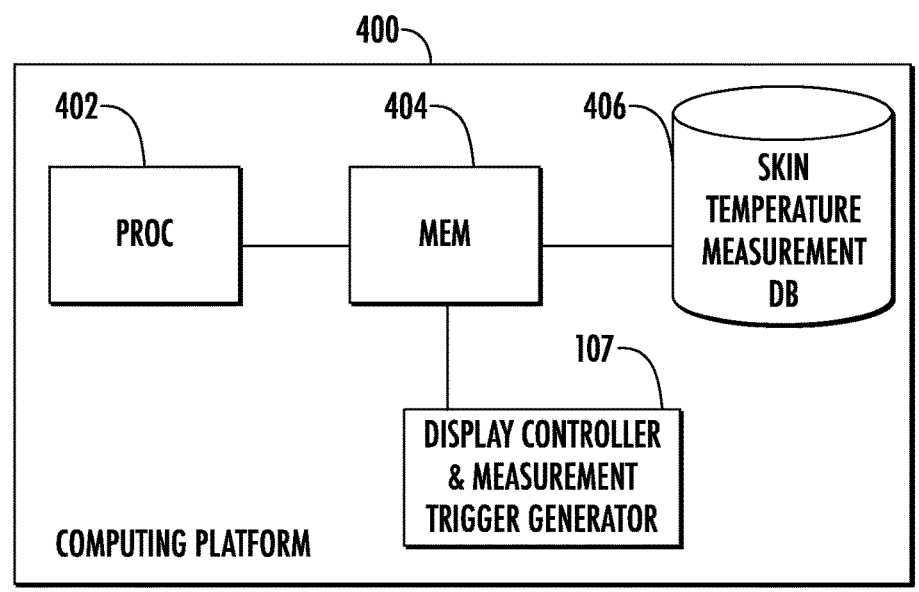
FIG. 4 is a block diagram illustrating an exemplary processing architecture of a system for obtaining accurate skin temperature measurements of subjects.

FIG. 4 is a block diagram illustrating exemplary software and hardware components of an exemplary system for obtaining accurate skin temperature measurements of subjects. In FIG. 4, the system includes a computing platform 400 that includes at least one processor 402 and memory 404. Computing platform 400 may be implemented on a printed circuit board located within housing 103. The system further includes display controller and measurement trigger generator 107 and a skin temperature measurement database 406. Display controller and measurement trigger generator 107 may be implemented in software executed by processor 402. Display controller and measurement trigger generator 107 receives video signals from camera 100, and generates control signals to control the display of visual alignment cues 108. Display controller and measurement trigger generator 107 also generates the trigger signal to trigger sensor 102 to obtain the skin temperature measurement and further generates output indicating results of the temperature measurement for display on display 106. Skin temperature measurement database 406 may store a history of skin temperature measurements obtained by sensor 102 in a given environment.

Figure 5A:
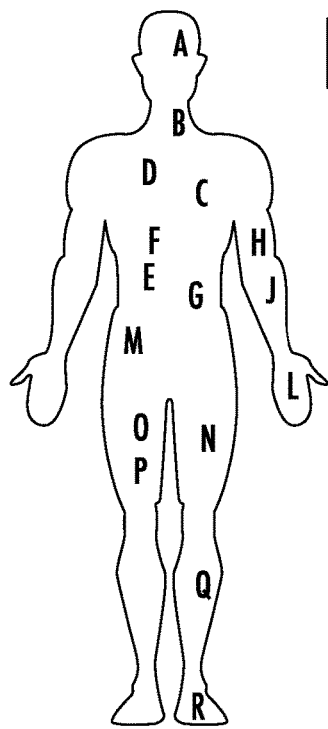
FIG. 5A is a table illustrating variance in skin temperature with ambient temperature.
Figure 5B:
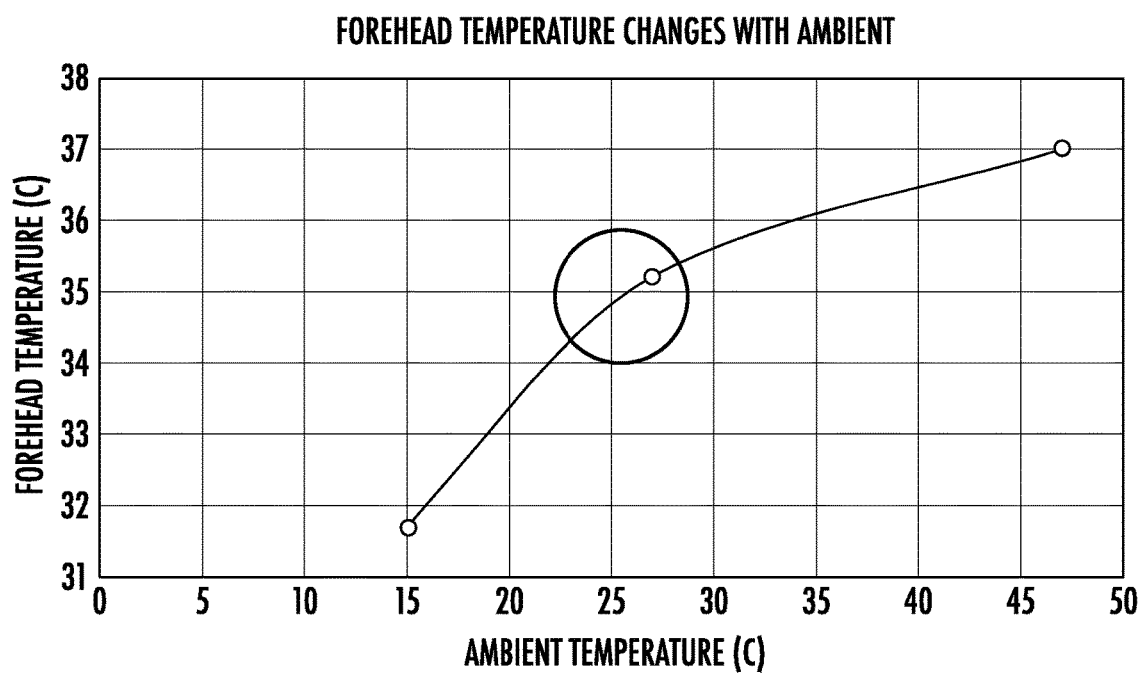
FIG. 5B is a graph illustrating changes in forehead temperature with changes in ambient temperature.

In one implementation of the subject matter described herein, display controller and measurement trigger generator 107 may be configured to output an absolute temperature measurement of the subject's skin temperature as measured by sensor 102. In another example, display controller and measurement trigger generator 107 may operate in relative mode to output whether a subject's temperature is normal with regard to the ambient temperature in a particular environment. As illustrated in FIGS. 5A and 5B, the skin temperature of a subject can vary with the ambient temperature of the environment in which the subject is located. In order to account for this, display controller and measurement trigger generator 107 may operate in a relative mode. Operating in the relative mode may include saving a predetermined number of temperature measurements for different subjects. For example, in relative mode, the last 30 skin temperature measurements obtained by sensor 102 may be recorded and stored in database 406. If the location of temperature sensor 102 is fixed for all 30 readings, display controller and measurement trigger generator 107 may determine an average of the stored measurements that represents a normal temperature for the environment. The average may be a moving average that is updated based on the last 30 temperature measurements.

When the temperature measurement is obtained for a given subject, rather than outputting the absolute temperature, the temperature may be compared to the moving average. If the difference between the measured temperature and the moving average is within a predetermined tolerance, the subject will be determined to have passed the screening. If the subject's skin temperature exceeds the moving average by more than the threshold amount, output may be generated indicating that the subject failed the screening. Additional screening and/or temperature measurements may then be performed.

In another example, the average ambient temperature of the environment may be recorded and that information may be used to perform a lookup in a lookup table to obtain a preconfigured average temperature for a particular environment. In such an implementation, if the subject's measured skin temperature exceeds the preconfigured average temperature by more than the threshold amount, display controller and measurement trigger generator 107 may generate output indicating that the subject failed the screening. If the subject's measured skin temperature does not exceed the predetermined average temperature by more than the threshold amount, display controller and measurement trigger generator 107 may generate output indicating that the subject passed the screening.

Figure 6:
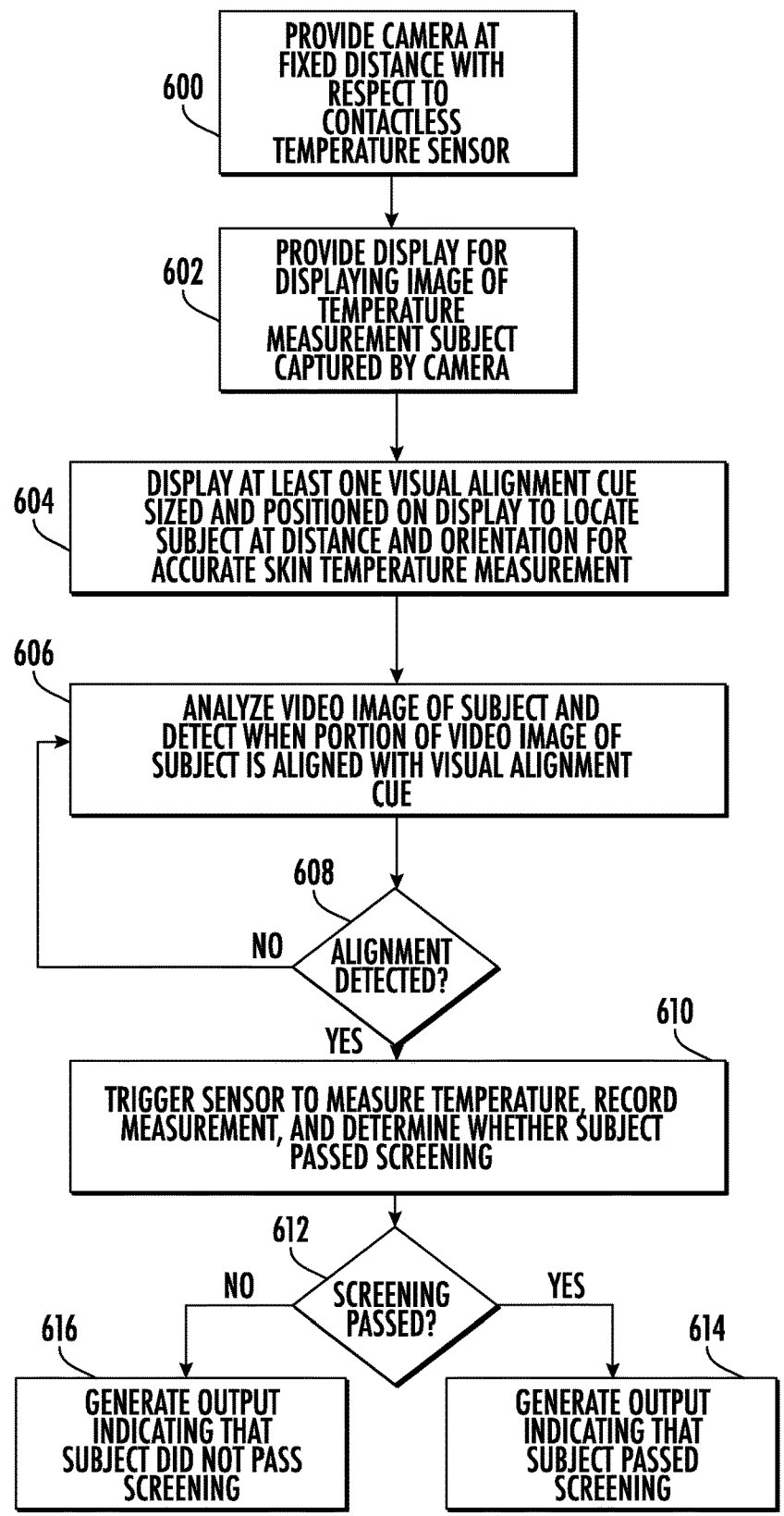
FIG. 6 is a flow chart illustrating an exemplary process for obtaining accurate skin temperature measurements of subjects.

FIG. 6 is a flow chart illustrating an exemplary process for obtaining accurate temperature measurements of subjects. Referring to FIG. 6, in step 600, the process includes providing a camera at a fixed distance with respect to a contactless temperature sensor. For example, a video camera 100 may be positioned in housing 103 at a fixed distance with regard to the field of view of a temperature sensor 102.

In step 602, the process includes providing a display for displaying a video image of a temperature measurement subject captured by the camera. For example, a video display, such as display 106 illustrated in FIG. 1, may be coupled to camera 100 to display a video image of the subject.

In step 604, the process includes displaying, on the display, at least one visual alignment cue that is sized and positioned on the display to locate the subject at a distance and orientation for accurate skin temperature measurement. For example, visual alignment cues, such as green circles or other shapes may be displayed on display 106 for aligning the subject's eyes, forehead, or other body part with the visual alignment cues. The visual alignment cues may be sized such that when the subject's eyes are aligned with the cues, the subject is located at the manufacturer-specified range or within a tolerance of the manufacture-specified range of the temperature sensor, where "range" refers to the distance from the temperature sensor to the subject in the axial direction (in the direction of line 300 in FIG. 3). The visual alignment cues may be positioned on the display as described above so that alignment of the subject's eyes with the visual alignment cue means that the subject's forehead is vertically and horizontally aligned with the field of view of the sensor.

In another example, rather than locating the visual alignment cues at a fixed position on the display, display controller and measurement trigger generator 107 may display, as the visual alignment cue, at least one moving virtual object, such as the circles illustrated in FIGS. 2A and 2B, that move while the display prompts the subject to move to maintain alignment with the visual alignment cues as they move. While the subject moves to maintain alignment of the subject's eyes with the visual alignment cues, display controller and measurement trigger generator 107 may trigger temperature sensor 102 to obtain multiple temperature measurements of the subject's skin temperature at different locations on the subject's forehead. Display controller and measurement trigger generator 107 may record the temperature measurements from the different locations on the subject, compute and average of the measurements, and store the average measurements as the skin temperature of the subject to be used for determining whether the subject has an elevated temperature. In one example, a peak skin temperature measurement is reported, where the peak skin temperature measurement is an average of the three highest skin temperature measurement obtained as the subject moves to maintain the alignment with the moving virtual object.

In step 606 and 608, the process includes analyzing the video image of the subject and detecting when the portion of the video image of the subject is aligned with the visual alignment cue. For example, display controller and measurement trigger generator 107 may detect when the subject's eyes are aligned with visual alignment cues 108. If the subject's eyes are not properly aligned with the visual alignment cues, control returns to step 606 where analysis of the displayed image for alignment continues until alignment is detected. If alignment takes longer than an operator-configured time period, the test may end, or the user may be prompted to try a different method for locating the measurement area of the subject's skin with the temperature sensor.

In step 608, if alignment is detected, control proceeds to step 610 where the process includes triggering the contactless temperature sensor to record a skin temperature measurement of the subject, recording the measurement, and determining whether the subject passed the screening. For example, display controller and measurement trigger generator 107 may trigger sensor 102 to obtain the skin temperature measurement when the subject's eyes are aligned with visual alignment cues 108, store the skin temperature measurement in skin temperature measurement database 406, and compare the measurement to the rolling average measurement or the average measurement obtained from the lookup table for the environment.

In step 612, it is determined whether the subject passed the skin temperature screening. If the measured temperature exceeds the average temperature by less than a threshold amount, the subject is determined to have passed the screening, and control proceeds to step 614 where display controller and measurement trigger generator 107 generates output indicating that the subject has passed the screening. As illustrated in FIG. 2B, in one example, the output may be a message displayed on display 106 indicating that the subject has passed the screening. In another example that will be described in detail below, display control and measurement trigger generator 107 may generate and send data to a printer associated with a kiosk that incorporates display 106 and computing platform 400 to print a badge indicating that a subject has passed the screening.

In step 612, if the measured temperature exceeds the average temperature by more than the threshold amount, control proceeds to sept 616 where display controller and measurement trigger generator 107 generates output indicating that the subject has failed the screening. As with the positive output in step 614, the negative output indicating that the subject failed the screening may be displayed on display 106 and/or printed in the form of a badge.

Figure 7:
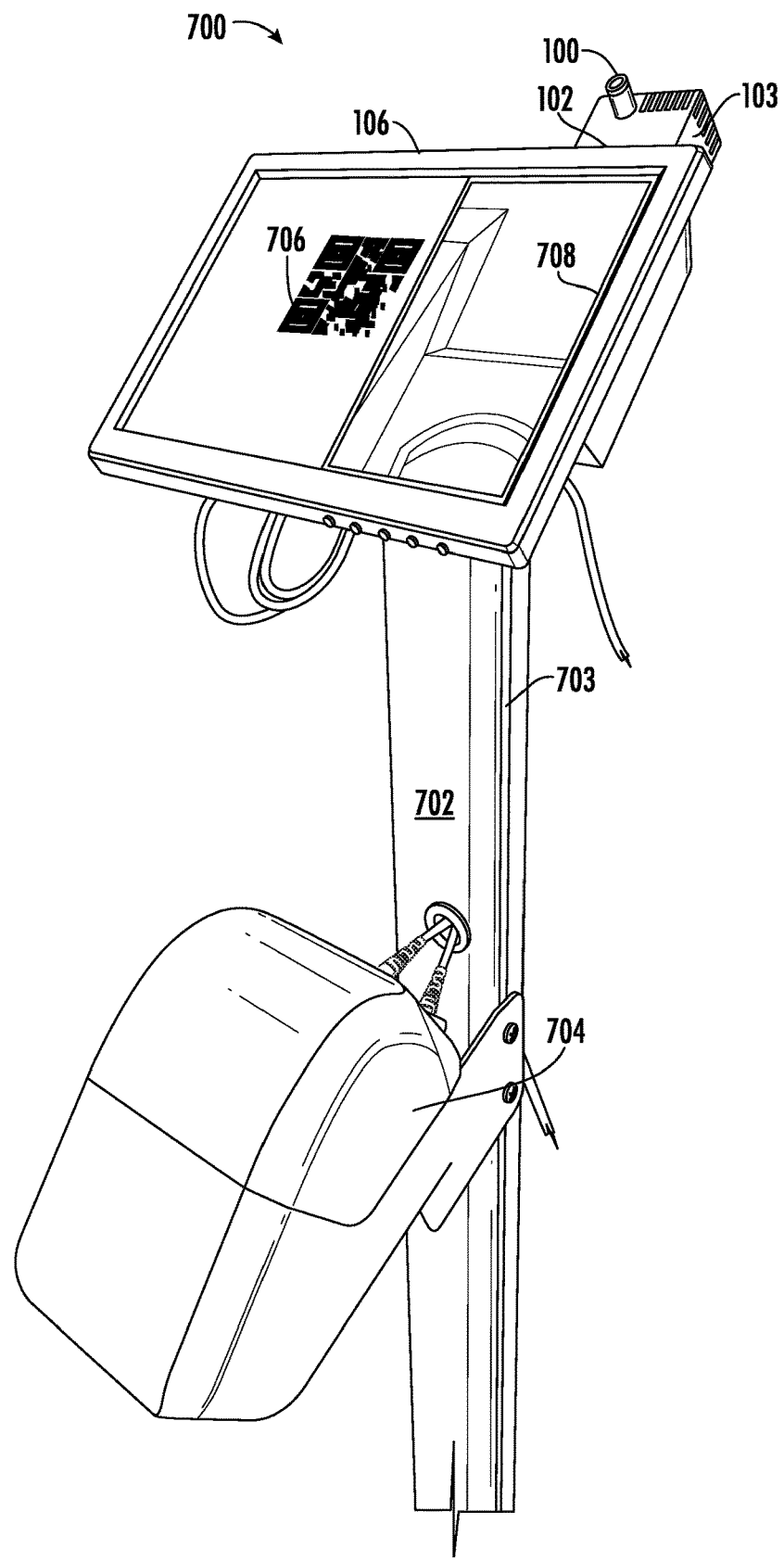
FIG. 7 is a perspective view of a free standing kiosk for obtaining accurate skin temperature measurements of subjects.

In one exemplary implementation, the system illustrated in FIG. 1 may include a free standing kiosk that is used to accurately obtain skin temperature measurements of subjects. FIG. 7 illustrates one example of such a kiosk. In FIG. 7, a kiosk 700 includes housing 103, display 106, camera 100, and temperature sensor 102 mounted on a stand 702. Housing 103 may include or enclose computing platform 400 as well as the electronic and optical components of camera 100 and sensor 102.

In the illustrated example, stand 702 is designed to be freestanding and also includes a track 703 for adjusting the height of components mounted to stand 702. Kiosk 700 further includes a printer 704 for printing badges indicating results of a subject's screening. For example, if a subject passes temperature screening, printer 704 may print a badge or other indicia indicating that the subject has passed screening and may also include the subject's name or other identifying information.

In one exemplary implementation, kiosk 700 may be without wireless communications capabilities and a subject may communicate with external entities using a mobile device, such as a mobile telephone. For example, display 106 may be configured to display a first quick response (QR) code 706 and may direct the user to scan QR code 706 using the subject's mobile device. Scanning QR code 706 will direct the subject's mobile device to connect to a website for obtaining identification and health information from the subject via a questionnaire. The website may encode the identification and health information for the subject in a second QR code and display the second QR code on the subject's mobile device. Display 106 may then prompt the subject to display the second QR code in blinking blue box 708 by placing the subject's mobile phone within the field of view of camera 100.

Placing the second QR code within the field of view of camera 100 may trigger display controller and measurement trigger generator 107 to read QR code, extract and store the health and identification information for the subject, and initiate the procedure for aligning the subject and recording the subject's skin temperature illustrated in FIGS. 1, 2A, and 2B. Once the subject's skin temperature is recorded, display controller and measurement trigger generator 107 may encode the skin temperature measurement and the health and identification information in a third QR, control display 106 to display the third QR code along with instructions for the subject to scan the third QR code using the subject's mobile device. When the subject scans the third QR code, the identity, health information, and skin temperature measurement may be uploaded to a database.

Figure 8:
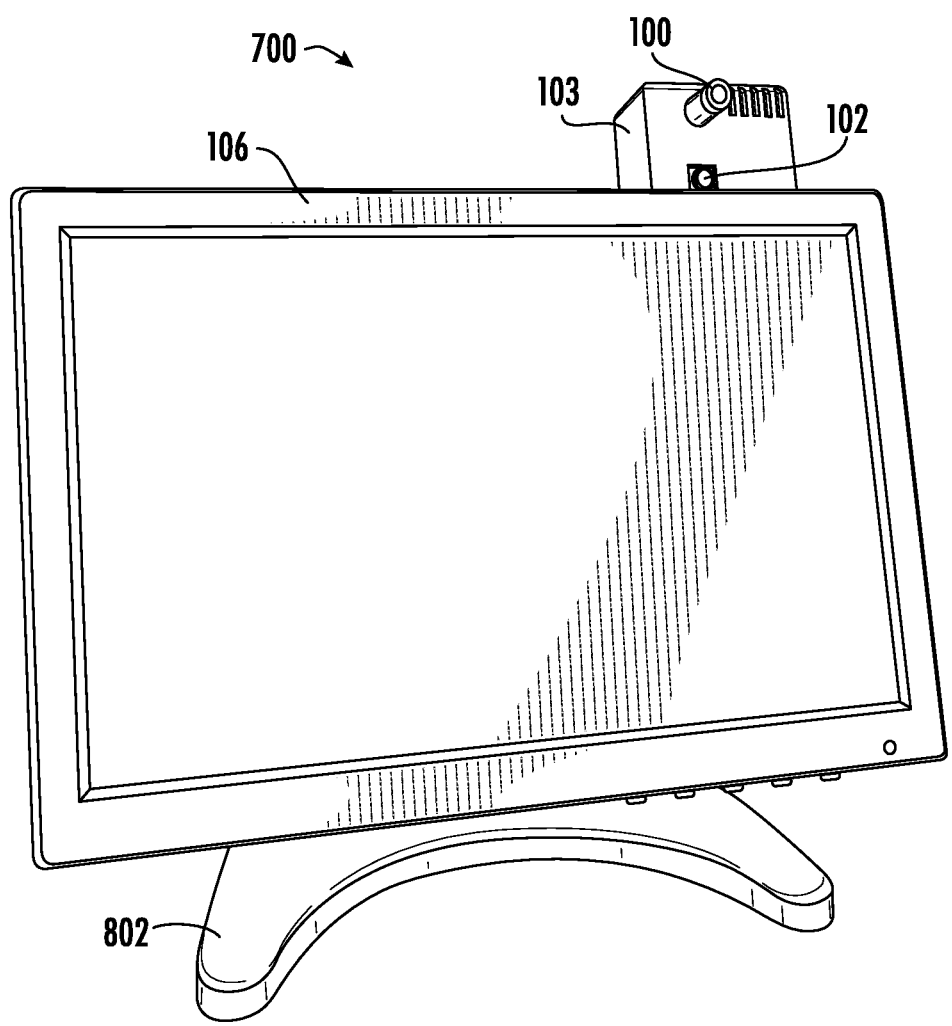
FIG. 8 is a front view of a tabletop kiosk for obtaining accurate skin temperature measurements of subjects.
Figure 9:
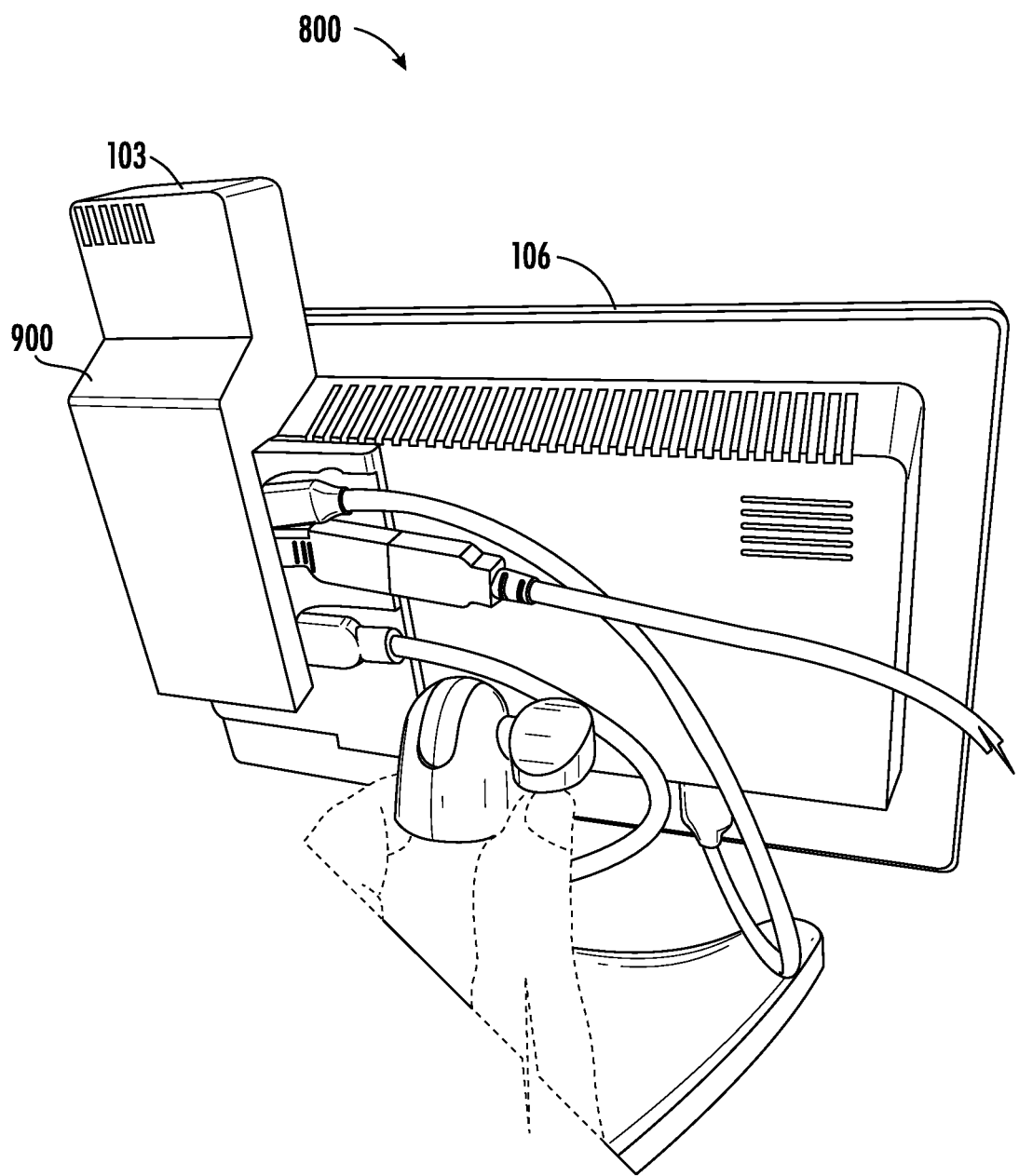
FIG. 9 is a rear view of the tabletop kiosk of FIG. 8 for obtaining accurate skin temperature measurements of subjects.

In the example illustrated in FIG. 7, kiosk 700 is a free standing device designed to be placed in the floor of a facility. In another example, the kiosk may be a free standing table top kiosk. FIG. 8 illustrates an example of a table-top free standing kiosk. In FIG. 8, kiosk 800 comprises a tabletop display where display 106 is mounted on a tabletop mount 802. Housing 103 that holds camera 100 and sensor 102 as well as computing platform 400 is connected to the rear of display 106, as illustrated in FIG. 9. In FIG. 9, housing 103 includes a bevel 900 that matches a bevel on the rear surface of display 106. Housing 103 also includes ports for connecting with power, display, and printer cables.

Figure 10:
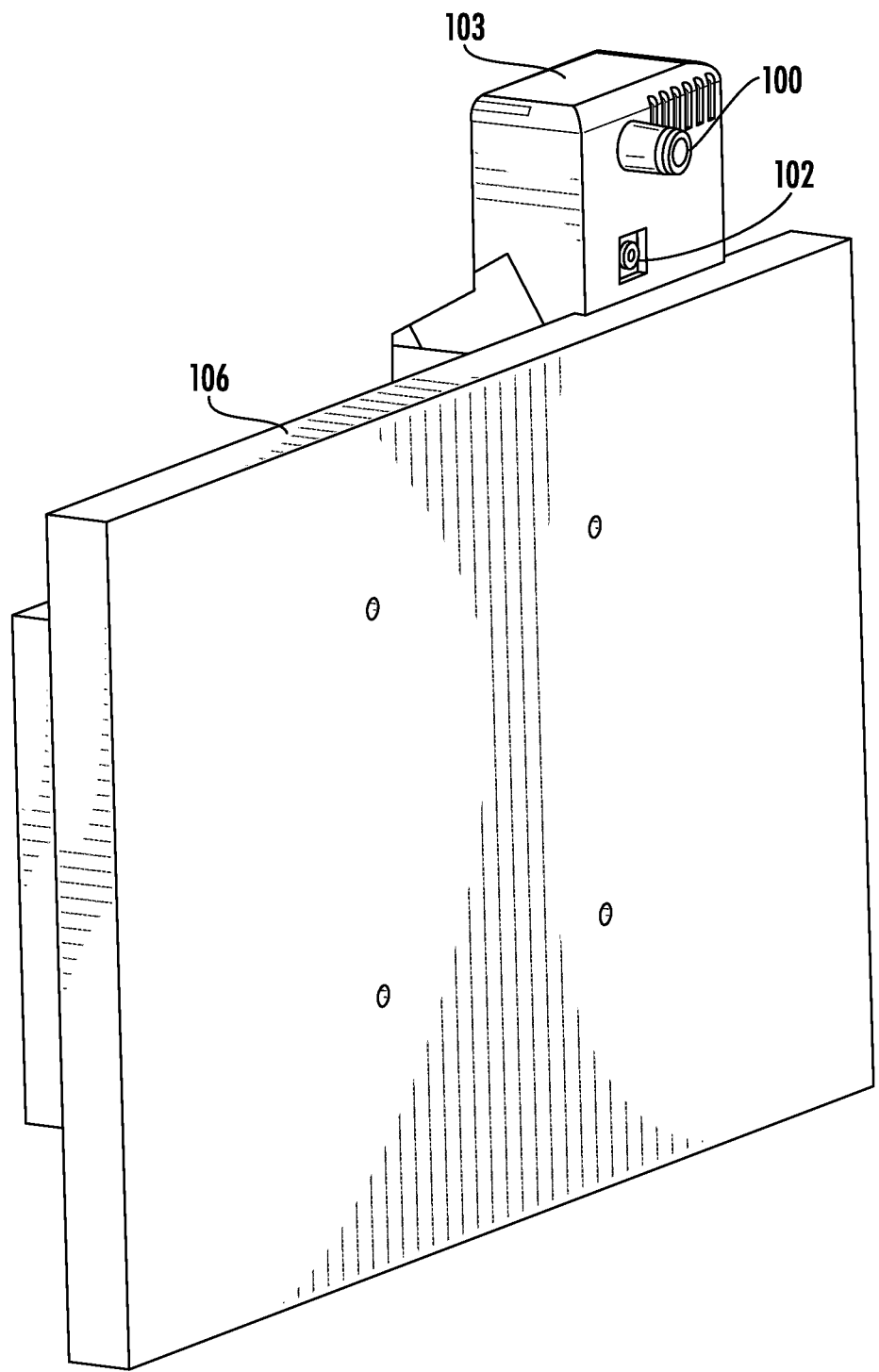
FIG. 10 is a perspective view of a model of a display and a camera and temperature sensor housing for obtaining accurate skin temperature measurements of subjects.

FIG. 10 is a front perspective view of a model of housing 103 and display 106. As with the example in FIGS. 8 and 9, housing 103 is configured to be mounted to a rear surface of display 106.

Figure 11:
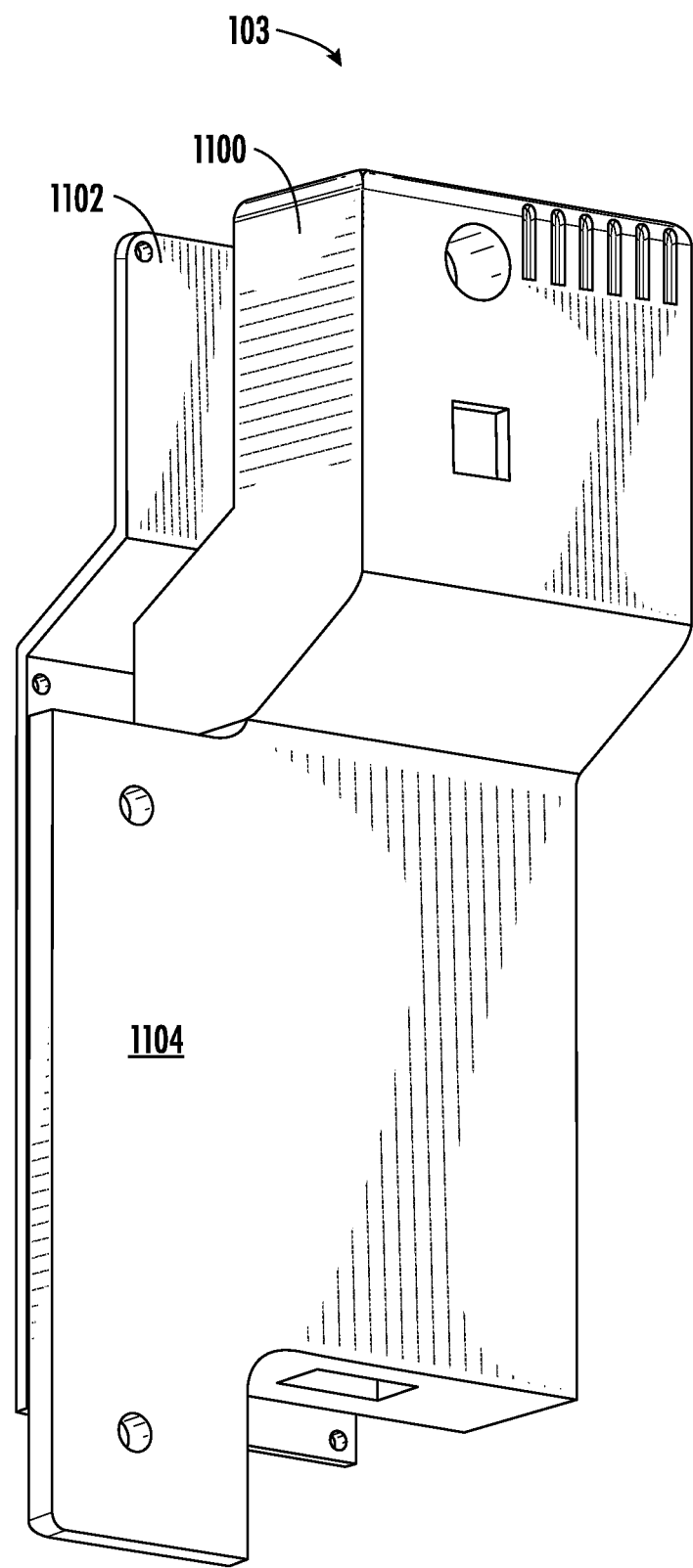
FIG. 11 is a front perspective view of the camera and temperature sensor housing of FIG. 10.

FIG. 11 is a partially exploded view of housing 103. In FIG. 11, housing 103 includes a front portion 1100 designed to enclose the camera, sensor, and electronics, and a matching cover 1102 that connects to front portion 1100 to form an enclosure. Housing 103 includes a mounting plate 1104 for mounting to the rear surface of display 106.

The subject matter described herein enables accurate temperature measurements using contactless temperature sensors, such as infrared temperature sensor. By forcing the user to put the user's eyes inside of the green circles (instead of just detecting a face) the subject matter described herein is able to get a better location information in terms of where the temperature sensor is pointing. Such an approach can be contrasted with approaches approach that do not control distances to the patient or account for pointing errors.

As described above, the subject matter described herein includes automatic detection of human eyes, when the user's eyes are aligned within the green circles, display controller and measurement trigger generator 107 may automatically detect the user's eyes. To reduce the likelihood of false eye detection, display controller and measurement trigger generator 107 analyzes the image and requires two eyes of a certain size, located an expected distance apart, both parallel within fixed limits, all designed to force the user into a specific spot in space.

Another aspect of the subject matter described herein includes is a failsafe. If the user's eyes cannot be detected in a certain time period, display controller and measurement trigger generator 107 instructs the user to hold the eyes still in a box drawn display 106. When the user holds the user's eyes within the box, display controller and measurement trigger generator 107 triggers temperature sensor 102 to record a temperature measurement. This failsafe may be needed for unusual cases (like a person with only one eye).

According to another aspect of the subject matter described herein, a method to detect the distance from the subject's face to the kiosk is provided. The distance can be detected using a sensor, such as a time of flight optical sensor or an ultrasonic distance sensor. Regardless of the type of proximity sensor used, once we have the distance from the subject's head to the kiosk, the following benefits can be achieved:

(1) We can detect when the patient is in front of the Kiosk to start the process of having the subject complete the questionnaire and recording the subject's skin temperature.

(2) The range data (the distance from the kiosk to the head) can be used to have a "Comfort" mode. Comfort mode means the user doesn't have to track their eyes and they can stand farther away from the kiosk and be comfortable. The range data can be used to correct or calibrate the fact that the subject is further from the sensor than the subject would be if the subject's eyes were aligned with the visual alignment cues.

Figure 12:
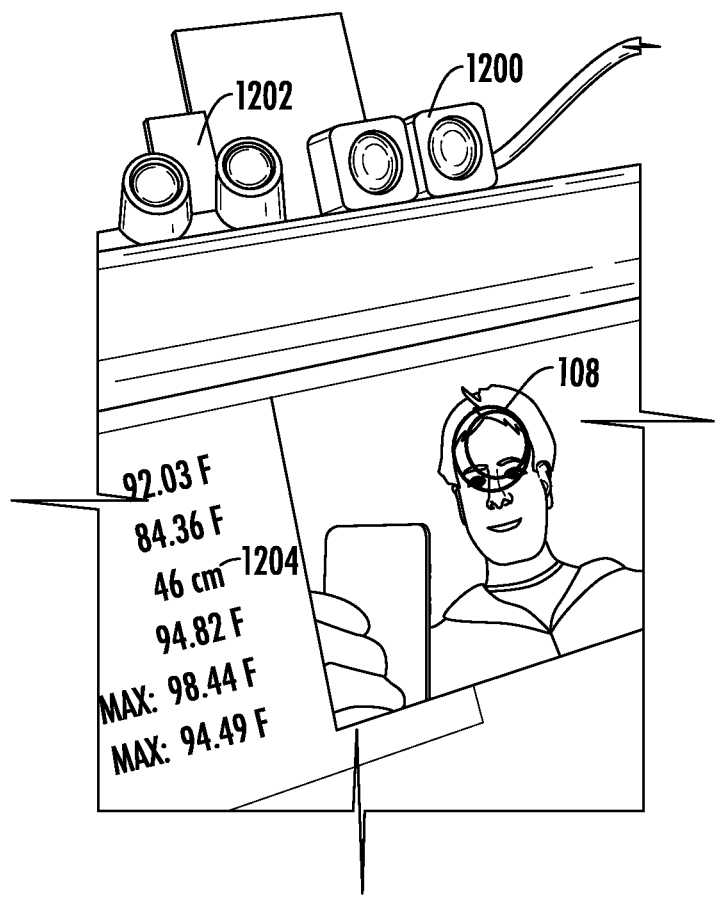
FIG. 12 is a diagram of a prototype implementation of a kiosk including range sensors.

FIG. 12 illustrates a prototype implementation of a kiosk with two different range sensors that may be used in combination with the camera and temperature sensor described above. In FIG. 12, the upper image shows range sensors 1200 and 1202 that may be co-located with the temperature sensor and the camera to record the range to the subject's forehead. The lower image shows the display of the image of the subject, with visual alignment cues 108 shown in green to indicate alignment of the subject's forehead with the field of view of the temperature sensor and the camera. Using one of range sensors 1200 and 1202, the kiosk outputs a range measurement 1204 that indicates the distance from the subject's forehead to the camera or temperature sensor. As indicated above, the range measurement can be used to trigger the routine for recording skin temperature measurements or to calibrate or correct skin temperature measurements with the subject is not with an optimal range of the temperature sensor for obtaining the skin temperature measurement.

According to another aspect of the subject matter described herein, the kiosk may be configured to operate in an equivalence mode in which a skin temperature measurement and another temperature measurement, such as an oral temperature measurement are obtained. An equation proprietary to the skin temperature manufacturer can be used to convert skin temperature measurement to another temperature measurement mode, such as an oral temperature measurement. The subject matter described herein improves the accuracy of equivalent mode temperature measurements computed using the manufacturer-provided equation. For example, one sensor manufacturer equation as well as most hand-held forehead thermometers use the term "Body Temperature". That is, the sensor reads the raw skin temperature and converts it to a higher number which they call "Body". For example, the sensor may read the skin (surface) to be 94.5° F. but report a "Body" temperature of 98.1° F. What they do not do is tell you exactly what part of the body this "Body" temperature represents.

Our studies allowed us to compare the so-called "Body" temperature to actual measurements made under the tongue by using an oral probe thermometer in both fast predictive and direct modes (oral thermometers often have two modes which were considered in this analysis). Once we established the difference between the forehead sensor's reported "Body" temperature and actual "Oral" values, we could provide an oral equivalence mode. According to the oral equivalence mode, the oral equivalence number is used with the average values from the table illustrated in FIG. 13 to compute the remaining equivalence modes including rectal, ear, core, and axillary. This results in user options for equivalence modes as shown in FIG. 14. The equivalence modes in FIG. 14 enable conversion between the skin temperature measurement and other body temperature measurement modes. For example, the conversion factor in FIG. 14 for oral equivalence mode is determined to be 0.56 F which means that by adding 0.56° F. to the measured forehead temperature (in degrees Fahrenheit), the measured forehead temperature can be converted to an equivalent oral body temperature measurement. The calculation of the equivalence modes may be performed by the display controller and measurement trigger generator 107 illustrated in FIG. 4.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for obtaining accurate skin temperature measurements, the method comprising:
    displaying, on a display, a video image of a temperature measurement subject captured by a camera;
    displaying, on the display, at least one visual alignment cue sized and positioned on the display such that when a predetermined portion of the video image of the subject is aligned with the at least one visual alignment cue, the subject is located at a predetermined distance and orientation for accurate skin temperature measurement by a contactless temperature sensor;
    analyzing the video image of the subject and detecting when the predetermined portion of the video image of the subject is aligned with the at visual alignment cue; and
    triggering the contactless temperature sensor to record a skin temperature measurement of the subject when the predetermined portion of the video image of the subject is aligned with the at least one visual alignment cue.

2. The method of claim 1 wherein the at least one visual alignment cue is sized such that alignment of the predetermined portion of the video image of the subject with the at least one visual alignment cue is indicative of the subject being at a distance from the contactless temperature sensor that is within a specified tolerance of the contactless temperature sensor for recording the skin temperature measurement of the subject.

3. The method of claim 1 wherein the at least one visual alignment cue is positioned on the display to vertically and horizontally align a portion of the subject's skin within a field of view of the temperature sensor.

4. The method of claim 1 comprising outputting the skin temperature measurement as an absolute temperature.

5. The method of claim 1 comprising determining an average skin temperature of a plurality of subjects in a given ambient environment, comparing the skin temperature measurement of the subject to the average skin temperature.

6. The method of claim 5 comprising generating output indicating that the subject possibly has a fever when the skin temperature measurement of the subject exceeds the average skin temperature by more than a threshold amount.

7. The method of claim 1 wherein displaying the at least one visual alignment cue for aligning at least a portion of the image of the subject with the visual alignment cue displaying virtual objects for aligning eyes of the subject with the virtual objects.

8. The method of claim 7 wherein the virtual objects comprise geometric shapes.

9. The method of claim 1 comprising displaying a visual indicator to the subject when the at least a portion of the image of the subject is aligned with the at least one visual alignment cue.

10. The method of claim 1 wherein displaying the at least one visual alignment cue includes displaying the at least one visual alignment cue as at least one moving virtual object, further comprising prompting the subject to move to maintain alignment between the predetermined portion of the image of the subject and the at least one moving virtual object, and wherein triggering the temperature sensor to obtain the skin temperature measurement includes triggering the temperature sensor to record plural skin temperature measurements as the subject moves to maintain the alignment.

11. The method of claim 10 comprising reporting a peak skin temperature measurement, wherein the peak skin temperature measurement comprises an average of a predetermined number of the skin temperature measurements having highest values.

12. The method of claim 1 comprising:
    displaying a first quick response (QR) code on the display for directing a mobile device of the subject to a website for obtaining identity and health information from the subject;

receiving, via the website and from the subject via the mobile device, the identity and health information;

encoding the identity and health information in a second QR code and displaying the second QR code on the mobile device;

reading, by the camera, the second QR code, and, in response, prompting the subject to initiate a process for allowing the contactless temperature sensor to obtain the skin temperature measurement of the subject;

encoding the skin temperature measurement and the identity and health information in a third QR code;

displaying the third QR code on the display;

prompting the subject to scan the third QR code using the mobile device; and in response to the subject scanning the third QR code, uploading the identity and health information and the skin temperature measurement from the mobile device to a database.

13. The method of claim 1 comprising providing a range sensor for measuring a distance between a skin temperature measurement region of the subject and the contactless temperature sensor.

14. The method of claim 1 comprising:

obtaining at least one additional body temperature measurement from the subject; and calculating, using the skin temperature measurement, the at least one additional body temperature measurement, and relationships between average body temperature measurements of different modes, at least one equivalence mode for converting the skin temperature measurement into at least one equivalent measurement of at least one body temperature measurement mode.

15. A system for obtaining accurate skin temperature measurements, the system comprising:

a housing;

a contactless temperature sensor located in the housing;

a camera located in the housing at a fixed distance with respect to the contactless temperature sensor;

a display for displaying a video image of a temperature measurement subject captured by the camera;

a computing platform including at least one processor and a memory; and a display controller and measurement trigger generator implemented by the at least one processor and configure to:

display, on the display, at least one visual alignment cue sized and positioned on the display such that when a predetermined portion of the video image of the subject is aligned with the at least one visual alignment cue, the subject is located at a predetermined distance and orientation for accurate skin temperature measurement by the contactless temperature sensor;

analyze the video image of the subject and detecting when the predetermined of the video image of the subject is aligned with the at visual alignment cue; and trigger the contactless temperature sensor to record a skin temperature measurement of the subject when the predetermined portion of the video image of the subject is aligned with the at least one visual alignment cue.

16. The system of claim 15 wherein the display controller and measurement trigger generator is configured to size the at least one visual alignment cue such that alignment of the predetermined portion of the video image of the subject with the at least one visual alignment cue is indicative of the subject being at a distance from the contactless temperature sensor that is within a specified tolerance of the contactless temperature sensor for recording the skin temperature measurement of the subject.

17. The system of claim 15 wherein the display controller and measurement trigger generator is configured to position the at least one visual alignment cue on the display to vertically and horizontally align a portion of the subject's skin within a field of view of the temperature sensor.

18. The system of claim 15 wherein the display controller and measurement trigger generator is configured to output the skin temperature measurement as an absolute temperature.

19. The system of claim 15 wherein the display controller and measurement trigger generator is configured to determine an average skin temperature of a plurality of subjects in a given ambient environment, comparing the skin temperature measurement of the subject to the average skin temperature.

20. The system of claim 19 wherein the display controller and measurement trigger generator is configured to generate output indicating that the subject possibly has a fever when the skin temperature measurement of the subject exceeds the average skin temperature by more than a threshold amount.

21. The system of claim 15 wherein the display controller and measurement trigger generator is configured to display, as the at least one visual alignment cue, virtual objects for aligning eyes of the subject with the virtual objects.

22. The system of claim 21 wherein the virtual objects comprise geometric shapes.

23. The system of claim 15 wherein the display controller and measurement trigger generator is configured to display a visual indicator to the subject when the at least a portion of the image of the subject is aligned with the at least one visual alignment cue.

24. The system of claim 15 wherein the display controller and measurement trigger generator is configured to display the at least one visual alignment cue as at least one moving virtual object, to prompt the subject to move to maintain alignment between the predetermined portion of the image of the subject and the at least one moving virtual object and to trigger the temperature sensor to record plural skin temperature measurements as the subject moves to maintain the alignment.

25. The system of claim 24 comprising wherein the display controller and measurement trigger generator is configured to report a peak skin temperature measurement, wherein the peak skin temperature measurement comprises an average of a predetermined number of the skin temperature measurements having highest values.

26. The system of claim 15 wherein the contactless temperature sensor comprises an infrared temperature sensor.

27. The system of claim 15 comprising a stand-alone kiosk lacking wireless connectivity and wherein the display and the housing are coupled to the display and the display controller and measurement trigger generator is configured to:

display a first quick response (QR) code on the display for directing a mobile device of the subject to a website for obtaining identity and health information from the subject;

read, from the camera, a second QR code including health and identification information received from the subject;

prompt the subject to initiate a process for allowing the contactless temperature sensor to obtain the skin temperature measurement of the subject;

encode the skin temperature measurement and the identity and health information in a third QR code;

display the third QR code on the display; and prompt the subject to scan the third QR code using a mobile device for communication from the mobile device to a database.

28. The system of claim 15 comprising a range sensor for measuring a distance between a skin temperature measurement region of the subject and the contactless temperature sensor.

29. The system of claim 15 wherein the display controller and measurement trigger generator is configured to obtain at least one additional body temperature measurement from the subject; and calculate, using the skin temperature measurement, the at least one additional body temperature measurement, and relationships between average body temperature measurements of different modes, at least one equivalence mode for converting the skin temperature measurement into at least one equivalent measurement of at least one body temperature measurement mode.

30. A non-transitory computer readable medium having stored thereon executable instructions that when executed by a processor of a computer control the computer to perform steps comprising:

displaying, on a display, a video image of a temperature measurement subject captured by a camera;

displaying, on the display, at least one visual alignment cue sized and positioned on the display such that when a predetermined portion of the video image of the subject is aligned with the at least one visual alignment cue, the subject is located at a predetermined distance and orientation for accurate skin temperature measurement by a contactless temperature sensor;

analyzing the video image of the subject and detecting when the predetermined portion of the video image of the subject is aligned with the at visual alignment cue; and triggering the contactless temperature sensor to record a skin temperature measurement of the subject when the predetermined portion of the video image of the subject is aligned with the at least one visual alignment cue.

* * * * *